US012186087B2

(12) United States Patent
Alkire

(10) Patent No.: US 12,186,087 B2
(45) Date of Patent: *Jan. 7, 2025

(54) EEG HEADPIECE WITH TRANSMISSION CAPABILITIES

(71) Applicant: Rhythmlink International, LLC, Columbia, SC (US)

(72) Inventor: Brian Alkire, Surprise, AR (US)

(73) Assignee: Rhythmlink International, LLC, Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/585,833

(22) Filed: Feb. 23, 2024

(65) Prior Publication Data

US 2024/0197232 A1 Jun. 20, 2024

Related U.S. Application Data

(63) Continuation of application No. 17/112,390, filed on Dec. 4, 2020, now Pat. No. 12,023,164, and a continuation of application No. 15/139,810, filed on Apr. 27, 2016, now Pat. No. 10,881,318, and a continuation of application No. 12/376,359, filed as application No. PCT/US2008/058467 on Mar. 27, 2008, now Pat. No. 9,345,418.

(Continued)

(51) Int. Cl.
*A61B 5/291* (2021.01)
*A61B 5/00* (2006.01)

(52) U.S. Cl.
CPC ............ *A61B 5/291* (2021.01); *A61B 5/0006* (2013.01); *A61B 5/6814* (2013.01); *A61B 2560/045* (2013.01)

(58) Field of Classification Search
CPC ..... A61B 5/291; A61B 5/0006; A61B 5/6814; A61B 2560/045
See application file for complete search history.

(56) References Cited

U.S. PATENT DOCUMENTS 3,896,790 A   7/1975  Dikmen
3,998,213 A   12/1976 Price
(Continued)

FOREIGN PATENT DOCUMENTS

DE  29505763 U1  6/1995
DE  19516659 A1  11/1996
(Continued)

OTHER PUBLICATIONS

International Search report (Aug. 18, 2008), 4 pages—PCT/US2008/058467.

(Continued)

*Primary Examiner* — Linda C Dvorak
*Assistant Examiner* — Abigail Bock
(74) *Attorney, Agent, or Firm* — Bryan L. Baysinger; Maynard Nexsen PC

(57) ABSTRACT

A headpiece, acquisition device, system and method for making electroencephalography (EEG) measurements. The EEG headpiece fits, or adjusts to fit, on a person's scalp, each of a plurality of electrodes is located in the headpiece corresponding to selected respective positions on the scalp, the electrodes are electrically connected to at least one electrical transmitter, and the headpiece is attached to the scalp after the electrodes have been located in the headpiece.

20 Claims, 11 Drawing Sheets

Related U.S. Application Data

(60) Provisional application No. 60/980,680, filed on Oct. 17, 2007, provisional application No. 60/949,772, filed on Jul. 13, 2007, provisional application No. 60/920,175, filed on Mar. 27, 2007.

(56) References Cited

U.S. PATENT DOCUMENTS

| | | |
|---|---|---|
| 4,395,820 A | 8/1983 | Sams |
| 4,967,038 A | 10/1990 | Gevins |
| 5,273,037 A | 12/1993 | Itil et al. |
| 5,293,867 A | 3/1994 | Oommen |
| 6,067,464 A | 5/2000 | Musha |
| 6,161,030 A | 12/2000 | Levendowski et al. |
| 6,510,340 B1 | 1/2003 | Jordan |
| 7,714,020 B2 | 5/2010 | Gluckman et al. |
| 9,345,418 B2 | 5/2016 | Alkire |
| 10,881,318 B2 | 1/2021 | Alkire |
| 2002/0091335 A1 | 11/2002 | John et al. |
| 2007/0238945 A1 | 10/2007 | Delic et al. |
| 2008/0306397 A1 | 12/2008 | Bonmassar et al. |

FOREIGN PATENT DOCUMENTS

| | | |
|---|---|---|
| DE | 10261342 A1 | 7/2004 |
| EP | 0541393 A1 | 5/1993 |
| WO | 2000045701 A1 | 8/2000 |
| WO | 2001043804 A1 | 6/2001 |

OTHER PUBLICATIONS

PCT Written Opinion of the International Searching Authority (Aug. 18, 2008), 6 pages—PCT/US2008/058467.

Aug. 15, 2011 Office Action in connection with U.S. Appl. No. 12/376,359.

Nov. 30, 2011 Office Action in connection with U.S. Appl. No. 12/376,359.

Apr. 10, 2012 Office Action in connection with U.S. Appl. No. 12/376,359.

Dec. 10, 2015 Office Communication concerning CA 2,682,060.

Sep. 4, 2018 Office Action in connection with U.S. Appl. No. 15/139,810.

Dec. 17, 2018 Office Action in connection with U.S. Appl. No. 15/139,810.

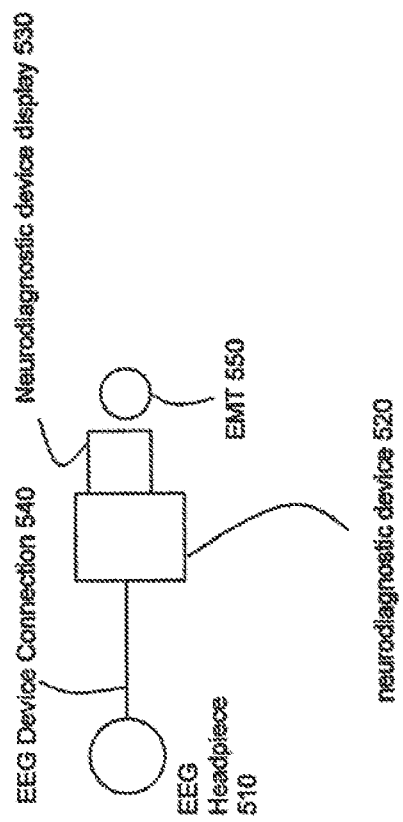

EEG HEADPIECE WITH TRANSMISSION CAPABILITIES

CROSS-REFERENCE TO RELATED APPLICATIONS

The present application is a continuation of currently pending application Ser. No. 17/112,390 filed on 4 Dec. 2020, which is a continuation of application Ser. No. 15/139,810 filed 27 Apr. 2016, which is a continuation of application Ser. No. 12/376,359 filed on 4 Feb. 2009, which is a US national stage of international application no. PCT/US2008/058467 filed 27 Mar. 2008, which claims the benefit of the filing dates of Provisional Appl. Ser. No. 60/980,680 filed 17 Oct. 2007, Ser. No. 60/949,772 fled 13 Jul. 2007, and Ser. No. 60/920,175 filed 27 Mar. 2007; the contents of all of which are incorporated herein by reference.

FIELD OF THE INVENTION

This invention relates to electroencephalography and, more particularly, to a headpiece, acquisition device, system and method for making electroencephalography measurements.

BACKGROUND OF THE INVENTION

The electroencephalogram (EEG) provides the medical practitioner with important information concerning brain activity. The EEG is commonly used in the clinical setting as a tool for diagnosing and monitoring epilepsy and syncope, sleep disorder, coma, and other manifestations of disorder or disease. Several practical limitations, however, have prevented widespread use of EEG technology in the urgent care setting.

One reason electroencephalography has not been in widespread use in the urgent care setting is the technical expertise needed to prepare the patient. In the conventional scalp EEG, electrode placement commonly conforms to the International 10-20 System. This reliable and reproducible system of electrode placement describes positioning of 24 electrodes with respect to the underlying section of cerebral cortex. Once identified, these electrode positions have typically been charted on the head of the patient by measurement with reference to the nasion, inion, and preauricular points. These positions are appropriately marked with a grease pencil or some other marking tool. Thereafter, the patient's scalp at each marked location may be prepared first by light abrasion and then by application of a conductive gel used to reduce impedance. An electrode is placed on the patient's scalp and secured by tape or collodion glue. Measurement and proper electrode placement of the full panel of 24 electrodes according to the 10-20 System may take up to an hour and requires considerable expertise as well as ideal clinical conditions.

Expertise is also required in properly mating the electrode transmitting wires with the EEG receiving console. A single transmitting wire is associated with each electrode. Each wire is commonly color coded to correspond with its proper location on the patient's scalp. A technician is presumed familiar with the color coding; otherwise a detailed legend or template is provided. Once the electrodes have been properly placed and secured to the patient's scalp, each colored wire must be plugged into a receiving console for perfecting the EEG measurement. Each wire must be plugged into a single corresponding port on the receiving console to ensure a proper EEG reading. In the event of transposition of one or several of the more than twenty transmitting wires of the typical setup, the technician must expend time determining which of the plurality of wires have been erroneously arranged.

In the process of manipulating and properly securing the wires to the receiving console, it is common for the electrodes to work themselves loose from the patient's scalp. Unfortunately, inadequate placement of an electrode frequently isn't detected until the technician attempts to obtain an EEG recording. For each unsecured electrode, the technician must re-prep the subject and then re secure the electrodes to the patient's scalp. Thereafter, after significant time expenditure, the recording process may commence.

Because of the technical and painstaking preparation required to obtain an EEG, a technician with expertise in the field is preferred, if not required. However, even where the technician preparing the conventional scalp EEG is highly specialized, time constraints are a second and substantial impediment to administration in the urgent care environment. Recent advances have helped to reduce the time impediment by describing workable modifications of the standard 10-20 System to allow for the use of fewer electrodes. Additionally, templates have been described that can be used to more easily identify appropriate electrode locations on the patient's scalp. Templates can save tens of minutes in setting up standard 10-20 System applications. These advances, while important improvements in the field, have not yet gone far enough to make urgent EEG a viable tool for frequent use.

One failing of available improvements is the failure to resolve the technically sensitive and lengthy process of electrode placement and interface problems associated with the securing of a plurality of electrodes to a patient's head and correctly plugging each transmitting wire into the proper corresponding port on a receiving console. In an urgent care environment, the careful precision and time needed to place electrodes at the proper location on the scalp and then correctly plug the transmitting wires into a receiving console wastes too much time and leaves too much room for error. Some devices employ color coding or other wire identification or location legends to guide the technician in properly placing a given electrode in a given identified electrode location. It is routinely left to the technician to harness the tangle of transmitting wires prior to ensuring proper attachment to the receiving console.

Finally, even if the technician is able to successfully traverse the difficulties associated with current systems, equipment requirements pose a final and significant impediment to urgent EEG. Once electrodes have been secured, equipment is necessary to receive, amplify and/or display the EEG information obtained from the patient. In the ambulatory setting, the need for this often cumbersome equipment is particularly limiting. Patient care is often occurring in an environment that does not allow for an umbilical from the patient to the receiving console. Instead, the patient must be mobile and able to be moved if necessary. In other cases, the required equipment is not proximate to the patient or has not been properly readied. In all these situations, it is therefore preferable that the portion of the EEG apparatus associated with the patient be independent of the receiving console such that transmission of the EEG signal can happen, when appropriate, wirelessly. Such flexibility would constitute a significant improvement.

Therefore, a new system is needed that further reduces the preparation time required to conduct an EEG measurement and the concomitant simplification of the setup procedure to allow EEG measurements by unskilled technicians. Preferably, these systems would utilize improved electrodes and allow, if desired, for concomitant EKG. An additional improvement is needed to allow for easy interface with a receiving console that is located in close proximity or remotely from the patient.

Advantages of certain exemplary aspects of the invention include the following. Embodiments of the invention can be used with different connections. For example, Urgent EEG Net to Amplifier; Urgent EEG to short range transmitter, then short range transmitter to amplifier; Urgent EEG Net to cell phone, then cell phone to Telemedx or BNI. Embodiments of the present invention increase accuracy by changing measurements symmetrically with increased head size, eliminating the possibility of erroneously mating electrode placement and jackbox placement, and using gold disk electrodes, which are the gold standard in EEG recording. Embodiments of the present invention increase speed of the process, by requiring no measurement, only one connection, and not involving tangled wires. Embodiments of the present invention also are cost effective. Because time is saved in multiple areas, cost is lessened. For example, no time is spent measuring. Time is also saved with one easy connection, as compared to making each individual connection. Time is also saved because the wires do not have to be untangled one at a time. They are all bound together in one cord. Also, the medical facility that does not have to employ a board certified electroencephalographer or a registered EEG technologist; instead, the record is sent to a reading facility. Cost to the hospital is also saved because EEG electrodes are patient billable. Further, if the EEG is sent via cell phone to a professional reading company, there is no need for the medical center to purchase expensive EEG machines. This will also make it easier to get approval from the administration allowing EEG labs to purchase new EEG equipment if needed. The main expense for the Urgent EEG Net system is realized on a patient by patient basis, and not all at once. This minimizes the need for administrative approval.

Embodiments of the present invention also improve patient care. There are not enough registered EEG technologists to cover all medical facilities. The Urgent EEG Net enables the unregistered medical professional to proficiently acquire an EEG record with gold cup electrodes. The Urgent EEG Net will allow hundreds of medical facilities who currently cannot provide adequate neurodiagnostic care, to do so. Also, faster application and faster connection means faster diagnosis and faster treatment in the ICU and ER. The Urgent EEG Net enables in-house staff to acquire the results of a study. The ICU physician has immediate access to a medical professional who can acquire an EEG, instead of waiting for the on-call tech to drive in with the results.

The Urgent EEG Net with Transmission Capabilities can serve the following markets and customers: ICU/ER; Small remote hospitals/medical facilities; the medical professional with no EEG experience; the EEG lab that needs new equipment, but cannot get approval; the EEG lab that wants to improve productivity; and the entire EEG market, with machineless EEG.

SUMMARY OF THE INVENTION

One embodiment of the present invention is directed to an electroencephalography system comprising a support structure that is adapted to cover at least predetermined areas on a patient's head when it is mounted on a patient's head, a plurality of electrodes that are mounted on the support structure so that, when the support structure is mounted on a patient's head, the electrodes are distributed around the patient's head and are capable of measuring usable electrical signals that are representative of electrical activity or activity in a patient's head, at least one connector having an output and an input, each of the plurality of electrodes being operatively coupled to the input of the connector so that, when the headpiece is mounted on a patient's head and when the electrodes are detachably coupled to the predetermined portions of a patient's head, electrical signals that are representative of electrical brain activity of the patient are sent to the output of the connector, and a first transmitter that is capable of being operatively coupled to the output of the connector.

Another embodiment of the present invention is directed toward to an electroencephalography system comprising a support structure that is adapted to cover at least predetermined areas on a patient's head when it is mounted on a patient's head, a plurality of electrodes that are mounted on the support structure so that, when the support structure is mounted on a patient's head, the electrodes are distributed around the patient's head and are capable of measuring usable electrical signals that are representative of electrical activity or activity in a patient's head, wherein each one of the plurality of electrodes are detachably coupled to the support structure, and at least one connector having an output and an input, each of the plurality of electrodes being operatively coupled to the input of the connector so that, when the headpiece is mounted on a patient's head and when the electrodes are detachably coupled to the predetermined portions of a patient's head, electrical signals that are representative of electrical brain activity of the patient are sent to the output of the connector, and a first transmitter that is capable of being operatively coupled to the output of the connector.

Another embodiment of the present invention is directed to a system wherein the support structure includes at least one strap.

Another embodiment of the present invention is directed to an electroencephalography system comprising a support structure that is adapted to cover at least predetermined areas on a patient's head when it is mounted on a patient's head, a plurality of electrodes that are mounted on the support structure so that, when the support structure is mounted on a patient's head, the electrodes are distributed around the patient's head and are capable of measuring usable electrical signals that are representative of electrical activity or activity in a patient's head, wherein each one of the plurality of electrodes are detachably coupled to the support structure, and at least one connector having an output and an input, each of the plurality of electrodes being operatively coupled to the input of the connector so that, when the headpiece is mounted on a patient's head and when the electrodes are detachably coupled to the predetermined portions of a patient's head, electrical signals that are representative of electrical brain activity of the patient are sent to the output of the connector, and a first transmitter that is capable of being operatively coupled to the output of the connector, wherein the first transmitter is mounted directly on the support structure.

Another embodiment of the present invention is directed to an electroencephalography system comprising a support structure that is adapted to cover at least predetermined areas on a patient's head when it is mounted on a patient's head, a plurality of electrodes that are mounted on the support structure so that, when the support structure is mounted on a patient's head, the electrodes are distributed around the patient's head and are capable of measuring usable electrical signals that are representative of electrical activity or activity in a patient's head, wherein each one of the plurality of electrodes are detachably coupled to the support structure, and at least one connector having an output and an input, each of the plurality of electrodes being operatively coupled to the input of the connector so that, when the headpiece is mounted on a patient's head and when the electrodes are detachably coupled to the predetermined portions of a patient's head, electrical signals that are representative of electrical brain activity of the patient are sent to the output of the connector, and a first transmitter that is capable of being operatively coupled to the output of the connector, and further comprising a second transmitter, the first transmitter being designed to send electrical signals representative of brain activity inside the patient's head to the second transmitter which is designed to retransmit the electrical signals to a remote location where the signals can be shown on a display and viewed by medical personnel.

Another embodiment of the present invention is directed to a system wherein a connector is adapted to convey electrical signals representative of an EEG measurement, audio signals, and/or an EKG measurement to its output.

Another embodiment of the present invention is directed to a system wherein each one of a plurality of electrodes comprise needle electrodes, disc electrodes or pronged electrodes.

Another embodiment of the present invention is directed to a system wherein each one of a plurality of electrodes is plated with stainless steel, platinum, ruthenium, silver, silver chloride, tin or gold.

Another embodiment of the present invention is directed to a system wherein each one of a plurality of electrodes comprises a plurality of prong points protruding from an electrode head, said prong points adaptable to be embedded in a patient's skin.

Another embodiment of the present invention is directed to an electroencephalography system comprising a support structure that is adapted to cover at least predetermined areas on a patient's head when it is mounted on a patient's head, a plurality of electrodes that are mounted on the support structure so that, when the support structure is mounted on a patient's head, the electrodes are distributed around the patient's head and are capable of measuring usable electrical signals that are representative of electrical activity or activity in a patient's head, wherein each one of the plurality of electrodes are detachably coupled to the support structure, and at least one connector having an output and an input, each of the plurality of electrodes being operatively coupled to the input of the connector so that, when the headpiece is mounted on a patient's head and when the electrodes are detachably coupled to the predetermined portions of a patient's head, electrical signals that are representative of electrical brain activity of the patient are sent to the output of the connector, and a first transmitter that is capable of being operatively coupled to the output of the connector, wherein the first transmitter comprises a wireless transmitter.

Another embodiment of the present invention is directed to a system wherein a support structure includes a chin support surface that is adapted to fit around the patient's chin.

Another embodiment of the present invention is directed to a system wherein a chin support is adjustable in order to fit a range of head sizes.

Another embodiment of the present invention is directed to an improved apparatus and method for obtaining an EEG from a patient in an urgent care environment including a disposable pre-formed Urgent EEG Net ("UEN"). The preformed UEN comprises a headpiece with recording electrodes incorporated therein. The headpiece is comprised of a plurality of straps with recording ports formed therein. The electrodes are associated with each of the plurality of recording ports and are attached or formed to the straps in a manner so as to present the recording head of the electrode to a corresponding recording port. In one embodiment, the electrodes are particularly amenable to use in an urgent care environment. The transmitting wires associated with each electrode are secured to the straps so as not to become entangled with one another or obscure or obfuscate recordation. The wires terminate at a common terminus which can be located, in one embodiment, at the apex of the headpiece.

The termini of the plurality of transmitting wires can be, for example, hardwired into a connector or a disposable transmitter. In the case of the connector, the connector may be mated with an EEG amplifying device or some other device designed to receive the EEG signal from the patient. Alternatively, the connector may be mated with a reusable or disposable transmitter.

A patient may be fitted with the UEN easily by the healthcare professional. The technician selects the appropriate UEN based on characteristics and parameters such as the age of the patient, the circumference of the patient's head, and the desired number of recording locations. Preferably, when selecting a UEN the healthcare profession will be cognizant of the fact that the distances between adjacent electrodes should ideally change between people with different head sizes and shapes.

In some cases, it is desirable for the technician to select a UEN that allows for concurrent or simultaneous recordation of an electrocardiogram (EKG). Depending on the environment and context, the technician may also select a UEN based on the availability of a receiving apparatus and/or amplifying device. The technician may select a UEN with a preformed disposable transmitter such that once the headpiece has been placed and the electrodes secured, the signal can be transmitted wirelessly to a receiving or amplifying device.

Alternatively, the technician may select a UEN with a pre-formed connector. The connector may be selected to mate with traditional EEG amplifying and receiving devise, or to a disposable or reusable transmitter. In the case of the disposable or reusable transmitter, the transmitter may be provided for in the UEN packaging and recycled after use (if appropriate) or be obtained separately from a source readily available.

Once the technician has selected the appropriate UEN package, the package is opened and the contents obtained. The patient's head is appropriately prepared prior to the headpiece being fitted to the patient. All the materials necessary for the preparation of the patient's head is contained in the Urgent EEG Net packaging. The headpiece will be adjusted to fit securely to the patient's head prior to preparation. The technician will ensure proper fitting of the headpiece prior to fitting the recording heads of the electrodes to the patient's skull.

The electrodes can be detachably coupled into the headpiece. Each electrode recording head is associated with a single recording port. The headpiece has been preassembled such that the recording head is clearly associated and presented at a single recording port location. The technician simply secures each recording electrode to the patient's head at the corresponding electrode port. Electrodes need not be color coded and no other form of technical coding is necessary to ensure proper electrode placement. Color coding, legends, or other forms of technical coding may be used, however, to reassure or reaffirm the color coding or legend system for technicians who may also be using conventional scalp EEG in non-urgent or emergent environments.

Once the electrodes have been placed, the technician is ready to begin transmission. While in prior systems the technician is required to plug the transmitting wires one by one into a receiving port that corresponds to the individual electrodes, the Urgent EEG Net is capable of being manufactured with the transmitting wires hard-wired into a connector or transmitting device. This obviates the need for the technician to painstakingly plug the wires into a connector, transmitting device, or EEG amplifier. In the Urgent EEG Net system, once the technician has attached the electrodes, the technician simply plugs in the connector to the mating connector and/or simply flips a switch to begin transmission.

BRIEF DESCRIPTION OF THE DRAWINGS

Further objects of the invention, together with additional features contributing thereto and advantages occurring therefrom, will be apparent from the following description of the invention when read in conjunction with the accompanying drawings; wherein:

FIG. 5 depicts a diagram of a system using an Urgent EEG net according to one embodiment of the subject invention.

DETAILED DESCRIPTION OF THE INVENTION

Figure 1A:
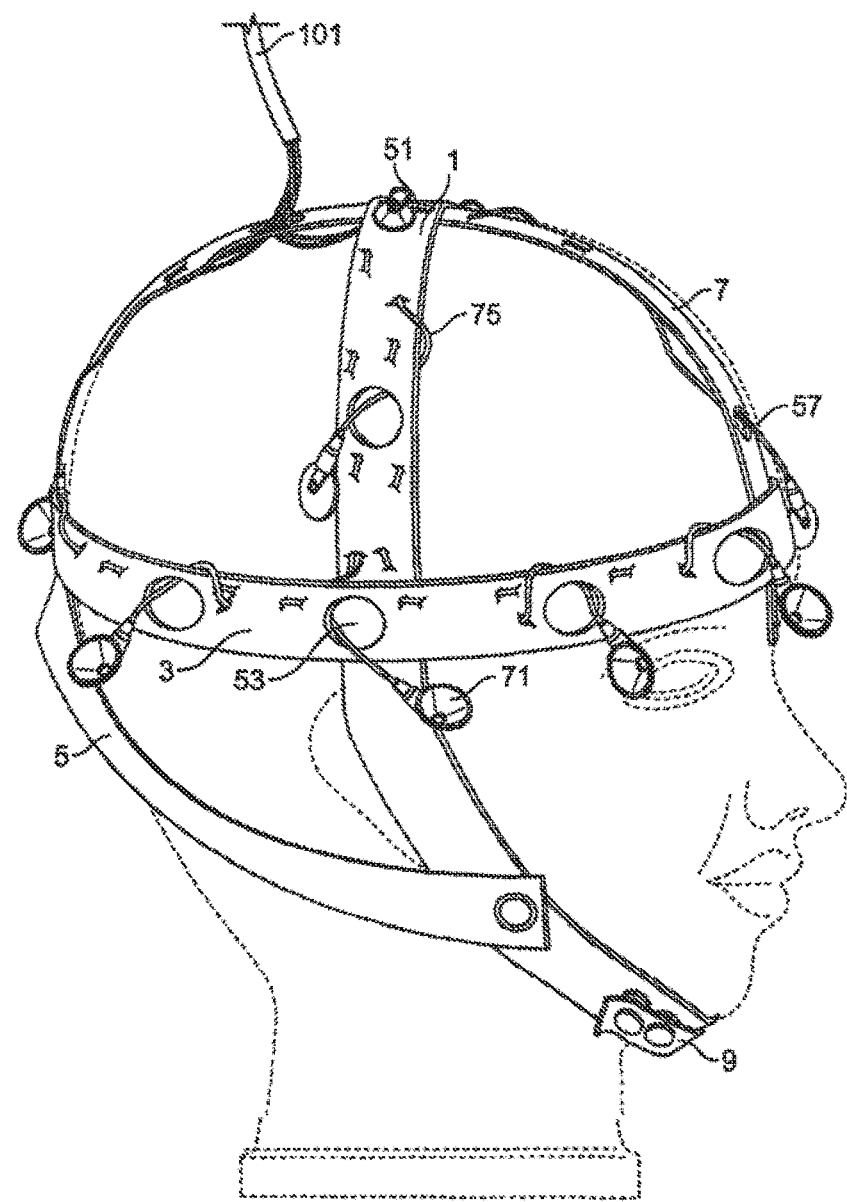
FIG. 1a depicts a side view of a headpiece according to one embodiment of the subject invention.
Figure 1B:
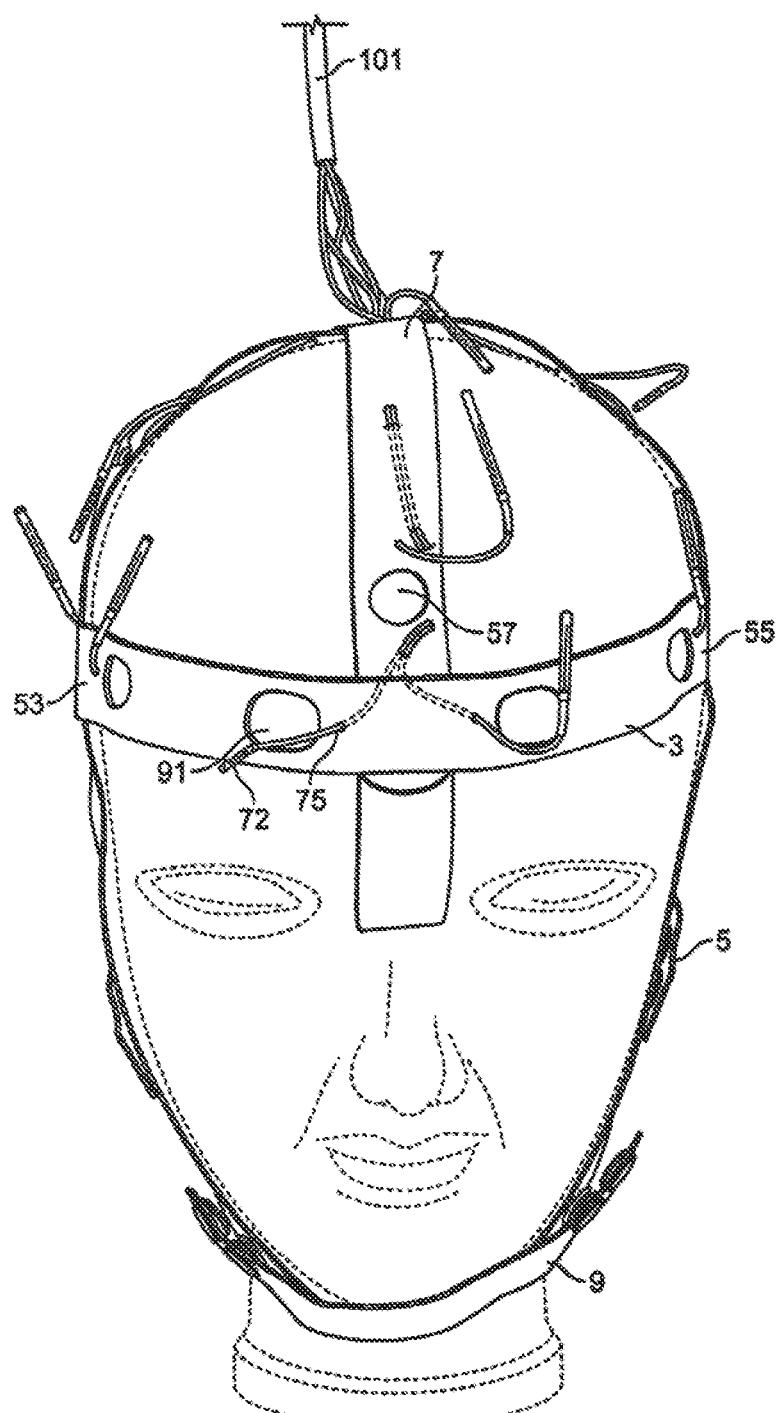
FIG. 1b depicts a frontal view of a headpiece according to one embodiment of the subject invention.
Figure 1C:
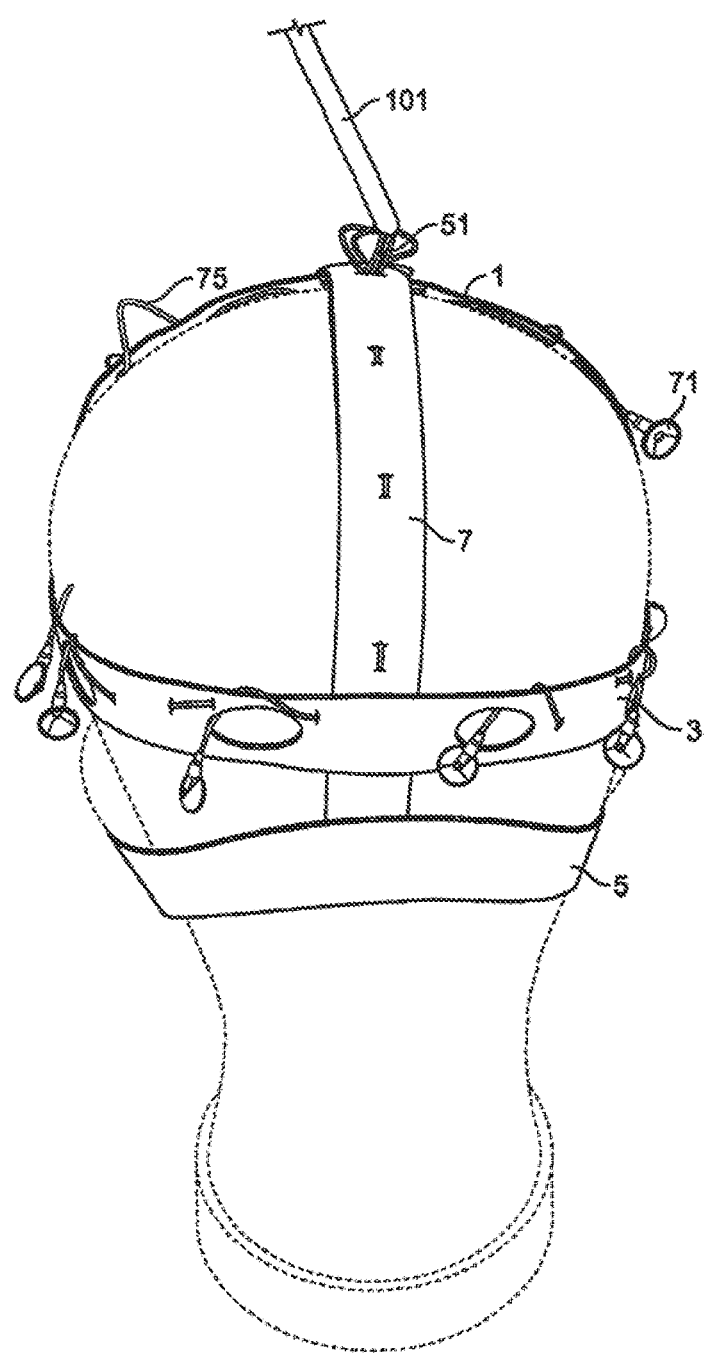
FIG. 1c depicts a rear view of a headpiece according to one embodiment of the subject invention.

Referring now to FIG. 1a, FIG. 1b and FIG. 1c, the headpiece of one embodiment of the EEG net is comprised of cloth straps. In a preferred embodiment of the invention, the headpiece includes transverse 1, circumference 3, posterior-tension 5, and anterior-posterior 7 straps comprised of a cloth material, preferably non-latex elastic material. A chin pad 9 may also be provided.

The transverse strap 1 of the headpiece has five holes each one centimeter in diameter. In a preferred embodiment, a first hole 51 is located at the apex of the headpiece or at the center of the transverse strap 1. On each side of the first hole 51, two additional holes are spaced equidistant from all adjacent holes. In a preferred embodiment of the invention, the transverse strap 1 is 1.9 centimeters wide and 61 centimeters long. The first hole 51 is located at the apex of the headpiece or at the center of the transverse strap 1. The plurality of holes are positioned such that each hole is approximately 6.3 centimeters from each adjacent hole. This distance between holes may be varied depending on the expected circumference range of a patient's head. Alternative embodiments are within the scope of the invention.

The transverse strap 1 is connected by sewing or other form(s) of attachment to a circumference strap 3 and an anterior-posterior strap 7. In a preferred embodiment of the invention, the circumference strap 3 includes ten holes one centimeter in diameter each. The circumference strap 3 is positioned so that a first 53 and second 55 hole correspond to the second of two holes on either side of the transverse strap 1. Four additional holes each are spaced on the front and rear portion of the circumferential strap 3. In a preferred embodiment of the invention, the circumferential strap is 1.9 centimeters wide and 51.5 centimeters long. The plurality of holes are spaced 4.9 centimeters from each adjacent hole. The circumference strap 3 overlaps with itself for 2.5 centimeters in such a way so as not to interfere with the opening of any one of the plurality of holes. Therefore, depending on the size of the patient's head, the strap may be enlarged or restricted.

An anterior-posterior strap 7 has anterior and posterior portions. The anterior-posterior strap 7 connects the front and back portion of the circumferential strap 3 and is also attached at the apex of the transverse strap 1. The anterior-posterior strap 7 includes two holes each one centimeter in diameter. A first hole is located at the apex of the headpiece or at the center of the anterior-posterior strap 7. This hole corresponds and overlaps with the first hole 51 of the transverse strap 1. A second hole 57 is located on the anterior portion of the anterior-posterior strap 7. In a preferred embodiment of the invention, the anterior-posterior strap 7 is 1.9 centimeters wide and 38.5 centimeters in length. The first hole is located at the apex of the headpiece 4 or at the center of the anterior-posterior strap 7. The second hole it located 7 centimeters from the anterior terminus of the anterior-posterior strap 7. Each end of the anterior-posterior strap 7 is sewn or otherwise secured at its terminus to the circumference strap 3 or to the tension strap 5.

A tension strap 5 is attached by sewing or other securing means to the circumference strap 3 and/or the transverse strap 1. The tension strap 5 provides headpiece stability and ensures and maintains proper positioning after the headpiece has been secured to the patient and during the EEG procedure. In a preferred embodiment of the invention the tension strap 5 is 1.9 centimeters wide and 36 centimeters in length. In a preferred embodiment, each end of the tension strap 5 is provided with Velcro or snaps such that the strap can be fastened to the transverse strap 1. The center of the tension strap 5 may be permanently attached to the posterior portion of the anterior-posterior strap 7 as shown in FIG. 1 although it is not necessary. In an assembled state, the tension strap 5 is positioned in such a manner so as not to obscure or obfuscate any of the holes in the transverse, circumference, and anterior-posterior straps 1, 3, and 7. Alternative attachments are within the scope of the invention.

The headpiece can be fitted with a chin pad 9 at the lower extent of the transverse strap 1. The chin pad 9 may be comprised of soft cloth material which is capable of conforming to the chin. In a preferred embodiment of the invention, each end of the transverse strap and each end of the chin pad will have Velcro or snaps attached, allowing the chin pad to be secured to the transverse strap in an adjustable manner. Alternative embodiments are consistent with the scope of the invention.

A UEN headpiece with the described straps will allow a technician to obtain an EEG recording from thirteen electrodes with an additional ground electrode incorporated. In an alternative embodiment, an additional hole may be placed 3 centimeters from the posterior of the vertex on the posterior-anterior strap. In some applications, institutions require an independent reference electrode to be used in obtaining an electroencephalogram reading. Additional optional reading locations are within the scope of the invention. Optional straps described below may also be used.

Figure 2A:
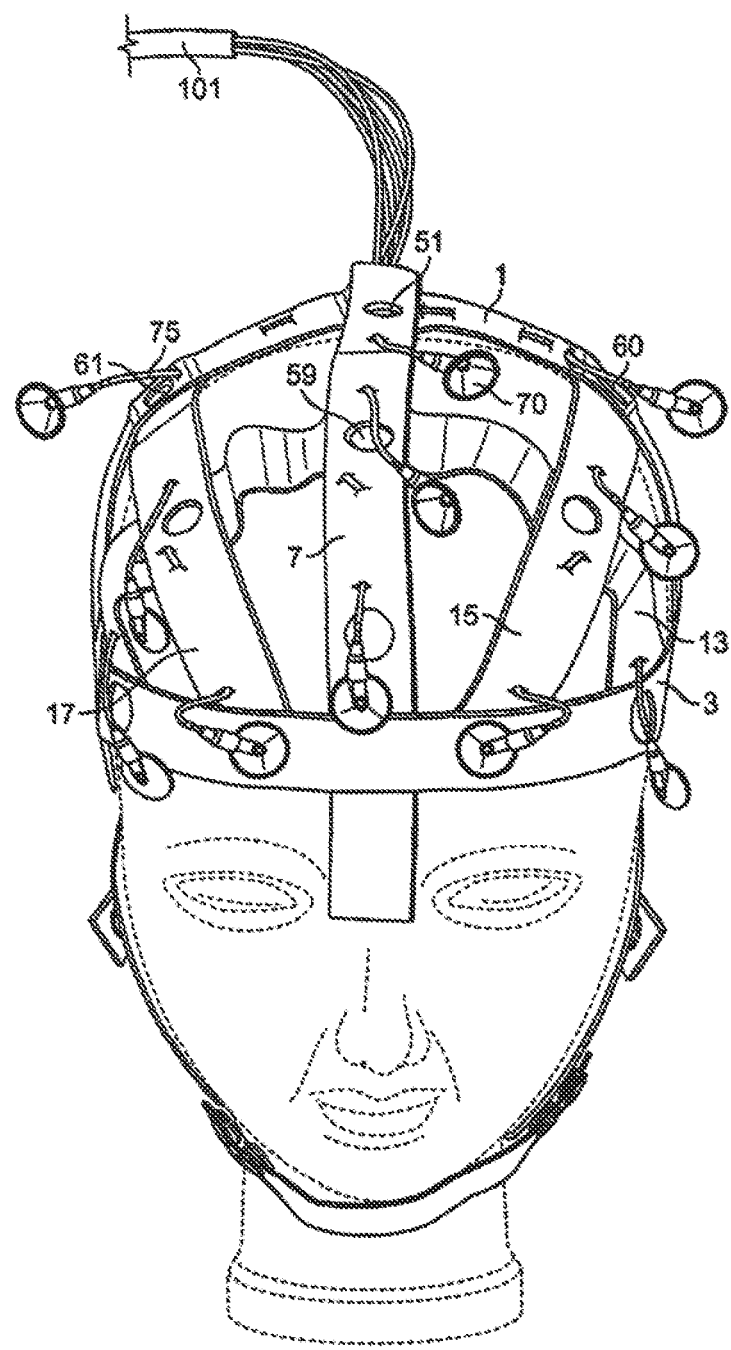
FIG. 2a depicts a frontal view of a headpiece with optional straps according to one embodiment of the subject invention.
Figure 2B:
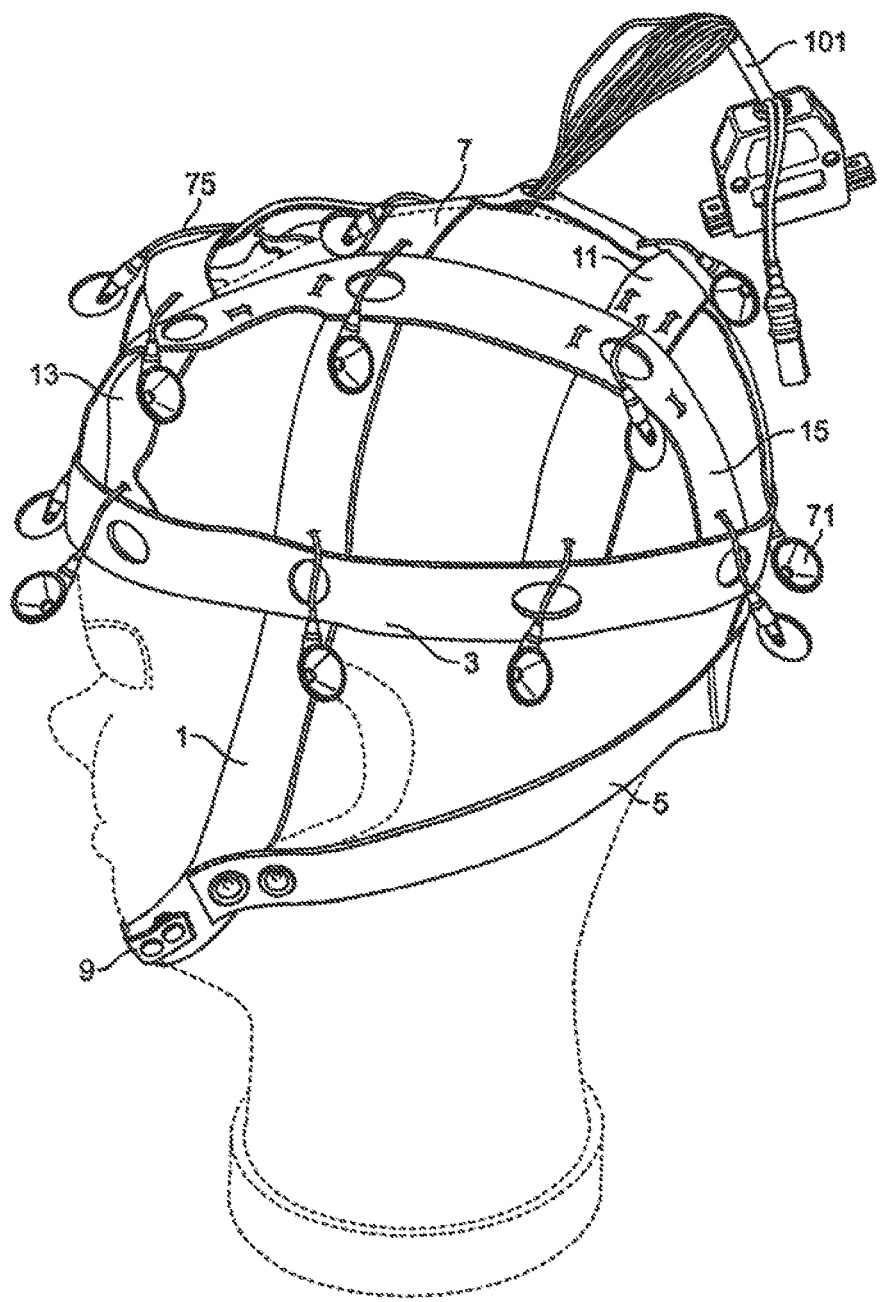
FIG. 2b depicts a side view of a headpiece with optional straps according to one embodiment of the subject invention.
Figure 2C:
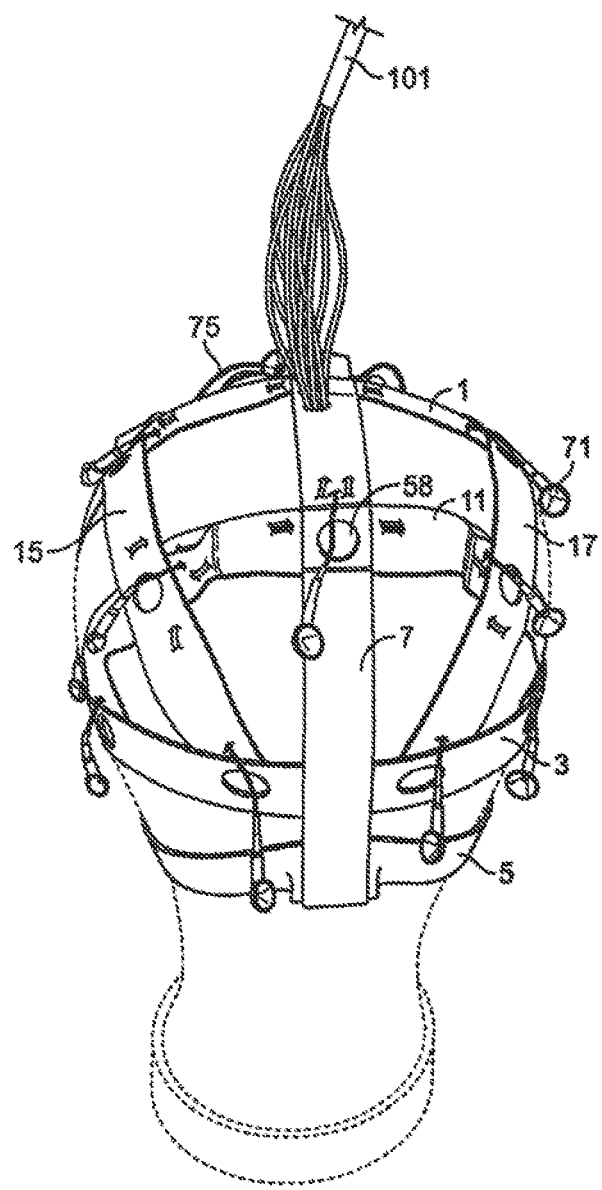
FIG. 2c depicts a rear view of a headpiece with optional straps according to one embodiment of the subject invention.

Referring now to FIG. 2a, FIG. 2b and FIG. 2c, the headpiece can be assembled with optional straps to accommodate additional electrodes. An optional parietal strap 11 is attached by sewing or otherwise securing it to the circumference strap 3 and the anterior-posterior strap 7. In a preferred embodiment, the parietal strap 11 has five holes each one centimeter in diameter. In a preferred embodiment, a first hole 58 is located at the center of the parietal strap 11. Two additional holes each are located on either side of the first hole 58 with all holes being equidistant from the adjacent hole. In a preferred embodiment, the parietal strap 11 is 1.9 centimeters wide and 26 centimeters long. The first hole 58 is located at the center of the parietal strap 11. The plurality of holes described are positioned such that each hole is approximately 6.3 centimeters from the nearest adjacent hole(s). To accommodate different sized heads, headpieces of differing sizes may be employed. Depending on how many straps and electrodes are desired, the desired number of electrodes would be incorporated into the desired number of straps and appropriately sized and spaced to make accurate EEG measurements on a patient.

An optional frontal strap 13 may also be used in addition to other optional straps or by itself. The frontal strap is attached by sewing or otherwise securing it to the circumference strap 3 and the anterior-posterior strap 7. The frontal strap 13 has five holes one centimeter in diameter each. In a preferred embodiment, a first hole 59 is located at the center of the frontal strap 13. Two additional holes each are located on either side of the first hole 59 with all holes being equidistant from the adjacent hole. For example, in a preferred embodiment of the invention, the frontal strap 13 is 1.9 centimeters wide and 26 centimeters long. The first hole 59 is located at the center of the frontal strap 13. The plurality of holes described are positioned such that each hole is approximately 6.3 centimeters from the nearest adjacent hole(s). Alternative embodiments may be employed depending on the expected circumference range of a patient's head.

One or two optional sagittal straps 15, 17 may also be used in addition to other optional straps or by themselves. The sagittal straps are attached by sewing or otherwise securing them to the circumference strap 3 and the transverse strap 1. The sagittal straps 15, 17 each have five holes one centimeter in diameter each. In a preferred embodiment, first holes 60, 61 are located at the center of the sagittal straps 15, 17. The first holes are positioned to coincide with the first hole on either side of the center hole 51 of the transverse strap 1 as shown, for example, in FIG. 2a. Two additional holes each are located on either side of the first holes 60, 61 with all holes being equidistant from the adjacent hole(s). For example, in a preferred embodiment of the invention, the sagittal straps 15, 17 are 1.9 centimeters wide and 26 centimeters long. The first holes 60, 61 are located at the center of the sagittal straps 15, 17. The plurality of holes described are positioned such that each hole is approximately 6.3 centimeters from the nearest adjacent hole(s). Alternative embodiments will be necessary depending on the expected circumference range of a patient's head, i.e. based on that patient's age. Alternative embodiments are within the scope of the invention.

A preferred embodiment of a headpiece of a UEN has been described. Referring now to FIG. 1 and FIG. 2, a single electrode is associated with each of a plurality of holes exposing the scalp of the patient when wearing the headpiece. In the headpiece of FIG. 1, there are 14 holes exposing the scalp of the patient and 14 electrodes associated with these holes. The electrodes associated with each hole are already incorporated into the UEN headpiece. For example, in FIG. 2a at the opening of a first hole 51 at the apex of the headpiece the head of an electrode 70 is available to be placed on the scalp of the patient once the headpiece has been secured in place.

Referring again to FIG. 1, a headpiece designed to accommodate 13 electrodes and a single ground electrode is depicted. Each hole corresponds to a recording location on the patient's scalp. A plurality of electrodes are associated with each recording port.

Figure 3A:
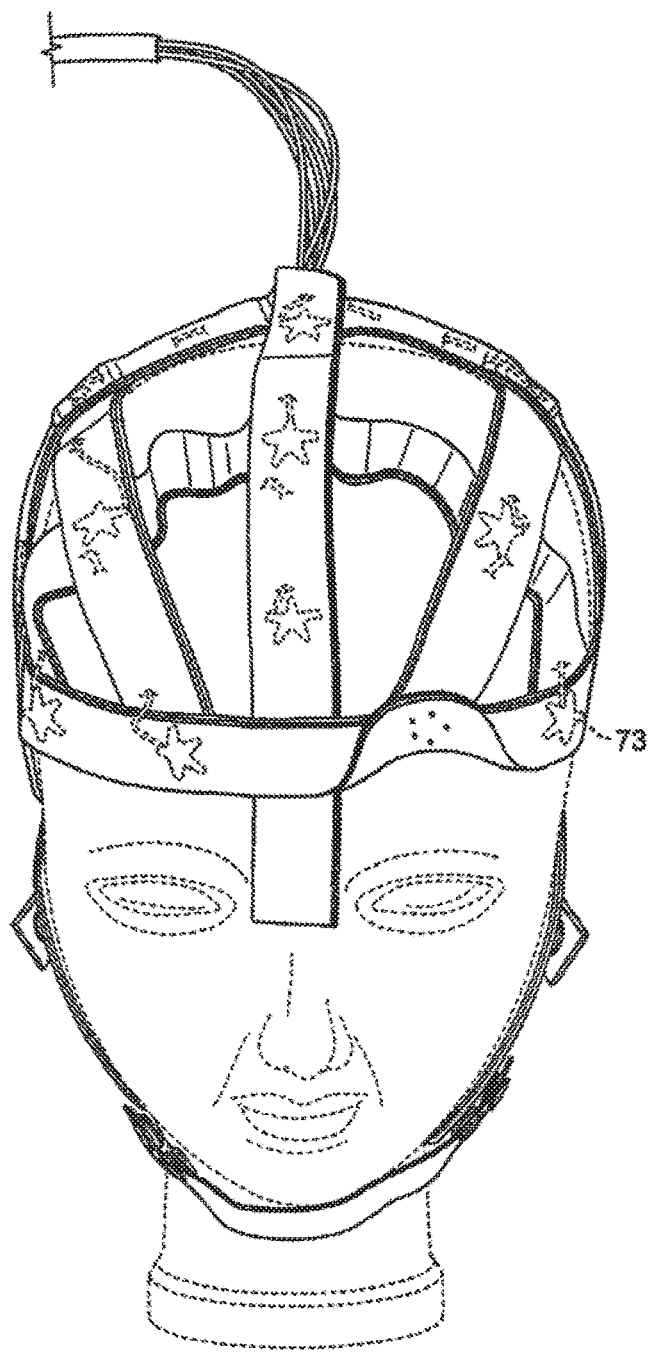
FIG. 3a depicts a frontal view of a headpiece with optional straps and an improved electrode amenable to use in the urgent or emergent care environment.

Referring now to FIG. 1, FIG. 2, and FIG. 3, each recording electrode is comprised of a receiving head connected to a transmitting wire 75. In a preferred embodiment of the invention, the receiving head is a disc electrode 71 as shown, for example, in FIG. 1a, FIG. 1c and FIG. 2. The electrode is plated with ruthenium, silver/silver chloride, or gold. In a most preferred embodiment of the invention, the disc electrode is plated with ruthenium. Ruthenium enhances the disposable nature of the electrode without compromising or degrading its conductive capacity. In an alternative embodiment of the invention the receiving head is a needle electrode as shown in FIG. 1b at 72. The needle electrodes preferably are comprised of pre-sterilized 10 millimeter stainless steel or platinum with a protective sheath.

Figure 3B:
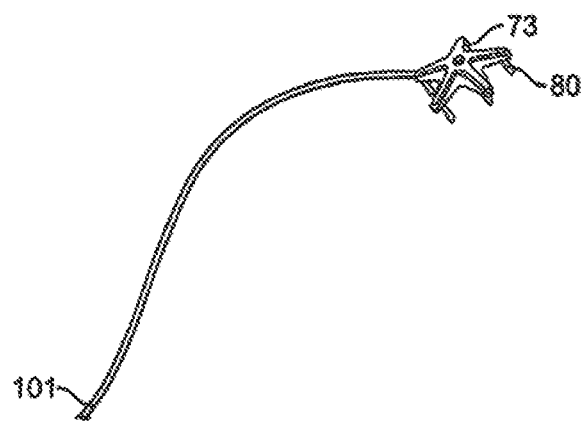
FIG. 3b depicts an improved electrode amenable to use in the urgent or emergent care environment.

Referring again to FIG. 3a and to FIG. 3b, an improved electrode amenable to use in the urgent or emergent care environment is shown. In an alternative embodiment of the invention, the receiving head 73 is a 5 pronged star shaped electrode which is fixated to the underneath portion of the net at the corresponding location. The electrode prongs 80 are plated with a highly conductive metal. In a preferred embodiment of the invention, the metal is ruthenium. Alternative embodiments include, but are not limited to gold, platinum, tin and silver/silver chloride.

The five-prong electrode is a non-prep, non-invasive improvement because each prong point 80 protrudes just enough from the base of the electrode head 73 to part the dead skin layer of the scalp without penetrating the living tissue beneath. A conductive gel may be used to provide a better conduction link as the electrode is being pressed through the gaps between the electrode and the living tissue.

Headpieces incorporating the five-prong electrode do not require the straps to have pre formed holes through which the technician inserts the electrode. In a preferred embodiment, a headpiece with pre-incorporated five prong electrodes comprised of elastic straps can be used to provide the necessary pressure required to press the electrodes into place once the headpiece has been properly placed on the patient's scalp. This improvement significantly reduces the preparation time in extremely urgent or critical applications. Other improved electrodes are being constantly developed and alternative electrodes are known in the art. It will be apparent to one skilled in the art that the present invention incorporates advantages and improvements that can be practiced regardless of the electrode system chosen. The present invention is not limited by or to the specific embodiments described.

Returning now to FIG. 1 and FIG. 2, the Urgent EEG Net headpiece is packaged with electrodes intimately associated with the straps. In FIG. 1*b*, used to highlight the features of the system, an electrode head 72 is presented at or near a single recording port 91. The electrode head 72 is fitted to allow for easy securing of the recording device to the scalp of a patient. In one embodiment of the invention, the transmitting wire 75 is sewn into the elastic fabric. In a preferred embodiment of the invention, the transmitting wire is sewn into the elastic band starting at or near the receiving head 72 and then follows the elastic straps before terminating at a terminal point 101 at the apex of the headpiece. In an alternative embodiment of the invention, the wire follows a channel to the recording port. It will be apparent to one skilled in the art that any means of securing the transmitting wire so as to prevent entanglement and to prevent the wire from interfering with the receiving head is within the scope of the invention. For example, the wires may be insulated in a manner to prevent interference by signals being transmitted in adjacent wires. The invention is not limited by the specific embodiments described herein.

Figure 4A:
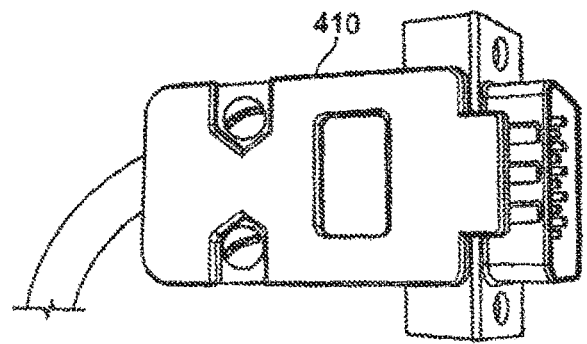
FIG. 4a depicts a hardwired multi-wire connector according to one embodiment of the subject invention.
Figure 4B:
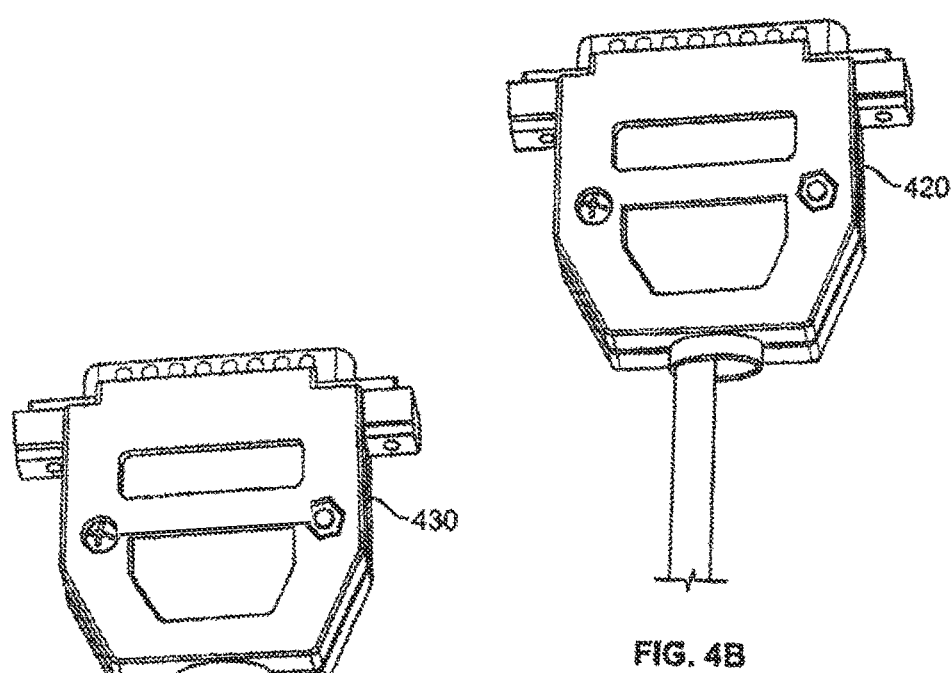
FIG. 4b depicts a hardwired multi-wire connector according to one embodiment of the subject invention.

Referring again to FIG. 1, FIG. 2 and FIG. 3, it is seen that the plurality of transmitting wires may terminate at a common terminus. Thus, for example, the terminal ends of the transmitting wires 101 terminate at an apex or vertex of the headpiece. The transmitting wire terminals are hard-wired to communicate with an EEG machine, a CPU transmitting unit, an electronic information storage device, a signal converter or any apparatus that may receive an EEG signal being transmitted according to any embodiment of the present invention. In a preferred embodiment, the terminal ends of the transmitting wires 101 are hard-wired into a connector. In a particular embodiment of the invention, the connector is a multi-wire connector with an input and an output as shown in FIG. 4*a* at 410 and FIG. 4*b* at 420. In an embodiment, the transmitting wires are connected to an input of the multi-wire connector, with the output of the multi-wire connector being mated to an EEG machine, a CPU transmitting unit, an electronic information storage device, a signal converter or any apparatus that may receive an EEG signal being transmitted according to any embodiment of the present invention. Alternatively, the terminal ends of the transmitting wires 101 can be connected directly to a DIN or other multi-pin connector. Other connecting options that would allow the terminal ends of the transmitting wires 101 to be connected directly or indirectly to an EEG amplifying apparatus or other electronic devices used in obtaining and/or processing EEG signals are consistent with the inventions described herein.

In alternative embodiments, the terminal ends of the transmitting wires 101 may be hardwired into a connector that may be mated with a non-disposable transmitting unit. Non-disposable transmitting units are known in the art. For example, the connector may be fitted to operate in conjunction with a Bio Radio, MQ-8, or P.E.T. Alternatively, the transmitter is disposable and there is no assembly or disassembly required to use and/or dispose of the UEN. The transmitter may be mounted directly onto the headpiece. In a preferred embodiment, the transmitter is a long-range transmitter that can communicate with a receiving device at a remote location. Receiving devices utilized in obtaining EEG signals are known in the art, for example, in U.S. Pat. No. 6,510,340. One skilled in the art will see that this embodiment of the invention may be practiced utilizing alternative direct and remote transmission of EEG signals and that such use is consistent with the scope of the present invention. Furthermore, the invention is not limited by specific embodiments described. An embodiment of the invention utilizing a transmitting unit and a long-range transmitter is shown in FIG. 5.

Figure 4C:
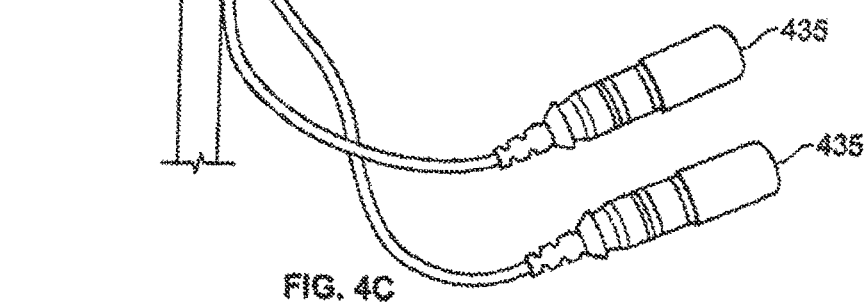
FIG. 4c depicts a hardwired multi-wire connector with two receiving ports for receiving transmitting wires from EKG electrodes according to one embodiment of the subject invention.

The UEN allows for optional concurrent EKG recordation. When optional EKG recordation is desired a UEN is selected with a connector that can receive up to eight transmitting wires from EKG electrodes. In FIG. 4*c*, at 430, a particular embodiment of the invention is disclosed wherein an optional connector for a UEN device is equipped with two receiving ports 435 for receiving transmitting wires from EKG electrodes. In alternative embodiments, an optional connector for a UEN device is equipped with as many as eight receiving ports for receiving transmitting wires from, for example, EKG electrodes, reference electrodes such as A1 and A2, and electrodes monitoring eye movements. One skilled in the art will understand that consistent with the scope of the invention a UEN device may be equipped with optional connectors to receive any transmitted signal information that is commonly obtained in the patient care environment. Furthermore, the scope of the invention is not limited by any description of particular embodiments contained herein.

A UEN has been described. The UEN may be packaged to allow for ease of use. In one embodiment of the invention, a disposable net package includes the net headpiece, incorporated electrode heads and trailing wires, a connector or transmitter, and all necessary accessories to allow for the securing of the net and electrodes to the head. For example, when disc electrodes are utilized, paste and prep in single use increments may be included. Q-tips or finger tip abrasion pads may also be provided. The packaging will clearly indicate the intended use of the contents. For example, the package will clearly indicate if the net is intended to fit a child or an adult. The packaging will also indicate the number of electrodes the apparatus will provide and whether or not the system allows for simultaneous recording of EKG. The invention is not limited by the specific packaging described.

In an exemplary embodiment, a template for use in electroencephalography comprises a headpiece, a plurality of electrodes, transmitting wires, and a connecting means. The headpiece comprises, for example, a circumference strap having a front portion, a back portion, a left portion, and a right portion, and a plurality of holes formed therein; a transverse strap having a plurality of holes formed therein, said transverse strap being having a left portion and a side portion, said left portion being secured to a left portion of a circumference strap, and said right portion being secured to a right portion of a circumference strap; an anterior-posterior strap having an anterior portion, a posterior portion, and a plurality of holes formed therein, said anterior portion secured to a front portion of the circumference strap, and said posterior portion being secured to a back portion of the circumference strap; a chin strap having a right and left portion and means for expanding or reducing the length of the chin strap; and a posterior tension strap having a back portion, a right portion, and a left portion, said left and right portion having means for securing the right and left portion of the posterior tension strap to a right and left portion of a transverse strap, and the back portion having means to secure it to the back portion of the anterior-posterior strap. The electrodes include a recording head and a transmitting wire, and one electrode is associated with one of the plurality of holes formed in the transverse strap, the circumference strap, and the anterior-posterior strap. The transmitting wires, for example, can be pre-incorporated and intimately associated with the straps and have a common termini. The termini of the transmitting wires can be, for example, hardwired into the connecting means. The connecting means can be, for example, positioned so as not to interfere with the recording electrodes or placement of the headpiece.

UEN template can also include, for example, an optional parietal strap comprised of a left portion, a right portion, and a plurality of holes formed therein, the right portion being secured to a left portion of a circumference strap, the left portion being secured to a left portion of a circumference strap.

A UEN template can also include, for example, an optional frontal strap comprised of a left portion, a right portion, and a plurality of holes formed therein, the right portion being secured to a left portion of a circumference strap, the left portion being secured to a left portion of a circumference strap.

The template also can include, for example, right and left sagittal straps, the straps having front and back portions, and a plurality of holes formed therein, the front portions being secured to the front of the circumference strap, the back portions being secured to the back of the circumference strap.

FIG. 5 depicts a diagram of a system using an Urgent EEG net according to one embodiment of the subject invention. FIG. 5 includes an EEG headpiece connected to neurodiagnostic device 520 by EEG device connection 540. FIG. 5 also includes neurodiagnostic device display 530 connected to neurodiagnostic device 520.

In operation, EEG headpiece 510 transmits EEG readings from the subject to neurodiagnostic device 520 over EEG device connection 540. EEG device connection 540 can be a wired connection. Alternatively, EEG device connection 540 can be a wireless connection. Any wireless connection capable of transmitting signals from EEG headpiece 510 to neurodiagnostic device 520 is within the scope of the invention.

Once neurodiagnostic device 520 receives the signals from EEG headpiece 510, it displays the readings on neurodiagnostic device display 530. An EMT 550 in the field can dynamically view the readings taken by EEG headpiece 510 on neurodiagnostic display device 530.

Figure 6:
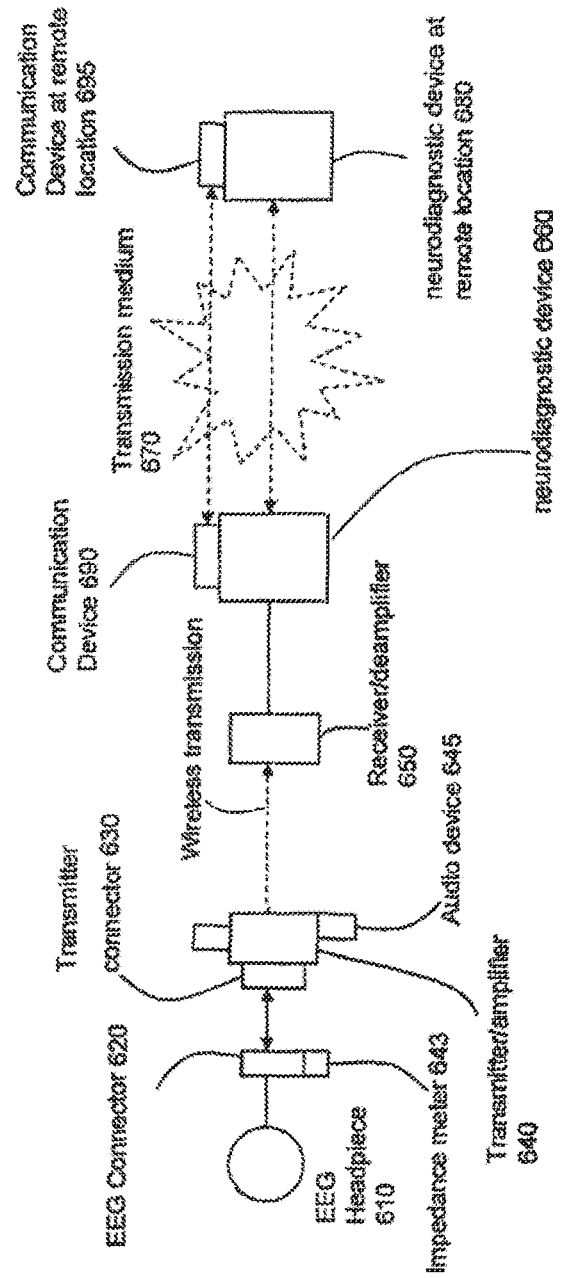
FIG. 6 depicts a system diagram of an Urgent EEG net using a wireless transmitter and in communication with a device at a remote location.

FIG. 6 depicts an embodiment of an urgent EEG net utilizing a transmitter. FIG. 6 includes an EEG headpiece 610 which is connected to an EEG connector 620. The EEG connector 620 can make a connection to a transmitter connector 630, which is connected to a transmitter-amplifier 640. Receiver deamplifier 650 connects to a neurodiagnostic device 660, which communicates with another neurodiagnostic device at a remote location 680 through a transmission medium 670.

In operation, EEG headpiece 610 reads EEG signals. The EEG signals are sent to a transmitter-amplifier 640 through a connection between EEG connector 620 and transmitter connector 630. EEG connector 620 can be a connector which is adapted to fit a standard neurodiagnostic connection, in which case transmitter connector 630 is a standard neurodiagnostic connector. Alternatively, EEG connector 620 can be any other standard or proprietary connector which is capable of transmitting signals read by EEG headpiece 610. Similarly, neurodiagnostic device 660 can be a standard neurodiagnostic device available in the art, a proprietary neurodiagnostic device, or another device that is adapted to read signals from an EEG headpiece 610. For example, neurodiagnostic device 660 may comprise, for example, a computer with appropriate software that is adapted to read signals from EEG headpiece 610. The computer may be equipped with a transmitting device, such as a wireless card, enabling it to transmit the EEG readings to a neurodiagnostic device at a remote location 680.

Transmitter amplifier 640 amplifies the EEG signals received from EEG headpiece 610 so the signals can be wirelessly transmitted to receiver-deamplifier 650. Receiver-deamplifier 650 deamplifies the received wireless signal to an amplification level that can be read by a standard neurodiagnostic device 660. Neurodiagnostic device 660, located at a close proximity to a patient wearing EEG headpiece 610, displays the neurodiagnostic readings to a user (not shown) without requiring a wired connection to EEG headpiece. This allows some flexibility in where neurodiagnostic device is physically located relative to EEG headpiece 610. For example, neurodiagnostic device 660 can be located in an adjacent room to a patient wearing EEG headpiece 610. In another embodiment, EEG headpiece 610 is worn by a patient in the field, as in an urgent care environment. In this embodiment, neurodiagnostic device 660 can be located near the patient, for example in an ambulance.

In FIG. 6, neurodiagnostic device 660 is also equipped with the ability to transmit the information received from the EEG headpiece 610 to a neurodiagnostic device at a remote location 680 through transmission medium 670. For instance, transmission medium 670 may be the Internet, or a wireless connection. This transmission allows a user at a remote location to read signals from EEG headpiece 610 even though the user is not located in a close proximity to a patient wearing EEG headpiece 610. For example, neurodiagnostic device 660 is located in an ambulance in the field, and while an Emergency Medical Technician (EMT) reads EEG data on neurodiagnostic device 660, it also transmits EEG data to neurodiagnostic device 680 located at a hospital miles away, so a doctor at the hospital can simultaneously view the EEG data and recommend the appropriate response. Both neurodiagnostic 660 and neurodiagnostic 680 may be equipped with a communication device so that a user using each device respectively can communicate with each other while viewing EEG data. This may or may not require a separate connection between communication devices through a transmission medium, which may or may not be the same medium as transmission medium 670.

Communication between neurodiagnostic device 660 and neurodiagnostic device at a remote location 680 may be bidirectional, so that information may be inputted into neurodiagnostic device at a remote location 680 and read by user using neurodiagnostic device 660.

Neurodiagnostic device 660 is also attached to communication device 690, which enables a user physically located in the vicinity of neurodiagnostic device 660 to communicate with a user physically located at remote location 680 and using communication device at remote location 695.

Communication device at remote location 695 is attached to neurodiagnostic device at remote location 680. Communication device 690 and communication device at remote location 695 are in communication through a transmission medium 670. In an alternative embodiment, communication device 690 and communication device at remote location 695 are in communication through a transmission medium that is different than transmission medium 670.

Depending on the method of transmitting signals to neurodiagnostic device at a remote location 680, neurodiagnostic device 660 may or may not require an amplifier to amplify the signal before transmitting brain wave signals to neurodiagnostic device at a remote location 680. Similarly, neurodiagnostic device at a remote location 680 may or may not require a deamplifier to deamplify the signal before reading the received transmission.

In an alternate embodiment, transmitter-amplifier 640 transmits directly to neurodiagnostic device at a remote location 680. Transmitter-amplifier 640 may employ any of a wide variety of transmitting technologies capable of transmitting neurodiagnostic signals from EEG headpiece 610 to a neurodiagnostic device at a remote location 680. As one example, transmitter-amplifier 640 may employ cellular technology in order to transmit neurodiagnostic signals. Depending on the transmitting technology employed, transmitter-amplifier 640 may not need to amplify any signal prior to transmission. In this embodiment, neurodiagnostic device 660 may or may not be present.

The urgent EEG net with transmission capabilities may be used to transmit information in addition to or instead of EEG neurodiagnostic signals in order to help skilled operators more accurately diagnose the patient's situation. Since the Urgent EEG Net may be operated by unskilled technicians in the field, skilled operators at a remote location may find it helpful to have additional information before assessing the patient's situation. This information would also be helpful to a skilled operator examining the EEG readings after they have been taken. For example, a patient may cough which would trigger a certain type of brainwave pattern. If the skilled operator saw the brainwave pattern without knowing that the patient coughed at a certain point, the skilled operator may be misled as to the patient's actual condition. Therefore, in one embodiment, the EEG net includes an audio device 645 adaptable to record a patient's responses during an EEG recording. Examples of such responses include coughing, seizures, or grinding teeth, but any other response by the patient is within the scope of the invention. Audio device 645 may be connected to transmitter-amplifier 640 so the audio data collected by the device may be transmitted with the EEG signal data if desired.

In one embodiment, an impedance meter 643 is used to verify the proper connection of the electrodes to the subject's head. The impedance meter 643 can be connected to transmitter-amplifier 240 through a connector, such as a DIN connector. Alternatively, the impedance meter 643 can be integrated with transmitter-amplifier 240. The impedance meter 643 may include a visual display that allows a user to quickly and easily determine which electrode is not properly connected.

In an alternate embodiment, neurodiagnostic device 660 does not transmit any long-term signal, and accordingly neurodiagnostic device at a remote location 680 is not present.

A specific embodiment of an Urgent EEG Net and a method of using the same according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

The invention claimed is:

1. An electroencephalogram (EEG) system comprising:
  a support structure that fits, or adjusts to fit, on a patient's head;
  a plurality of electrodes, the plurality of electrodes mounted on the support structure so that when the support structure is placed on the patient's head, the plurality of electrodes are distributed around the patient's head, and the plurality of electrodes are capable of receiving and measuring one or more signals representative of brain activity;
  a plurality of transmitting wires incorporated into the support structure; and
  a multi-wire connector having an input and an output, where each of the plurality of transmitting wires is operably connected between a respective electrode and the input of the multi-wire connector.

2. The system of claim 1, further comprising a neurodiagnostic device, wherein the output of the multi-wire connector is configured to be operatively coupled to the neurodiagnostic device and the neurodiagnostic device is configured to receive the one or more signals.

3. The system of claim 2, wherein the neurodiagnostic device is configured to display information corresponding to or derived from the one or more signals.

4. The system of claim 2, wherein the neurodiagnostic device comprises a wireless transmitter configured to transmit one or more signals received by the neurodiagnostic device to a remote location, the signals representative of brain activity.

5. The system of claim 1, wherein each of the plurality of electrodes are positioned at predetermined locations on the support structure.

6. The system of claim 1, wherein each of the plurality of electrodes is detachably coupled to the support structure.

7. The system of claim 1, further comprising a wireless transmitter, wherein the output of the multi-wire connector is configured to be operatively coupled to the wireless transmitter, the wireless transmitter being capable of transmitting the one or more signals.

8. The system of claim 7, further comprising a neurodiagnostic device, wherein the wireless transmitter is configured to transmit the one or more signals to the neurodiagnostic device, and the neurodiagnostic device is configured to display information corresponding to or derived from the one or more signals.

9. The system of claim 1, wherein the support structure is adapted to cover at least predetermined areas of the patient's head when it is mounted on the patient's head.

10. The system of claim 1, further comprising an impedance meter configured to verify connection of the plurality of electrodes to the patient's head.

11. An electroencephalogram (EEG) system comprising:
  a support structure that fits, or adjusts to fit, on a patient's head;
  a plurality of electrodes, the plurality of electrodes mounted on the support structure so that when the support structure is placed on the patient's head, the plurality of electrodes are distributed around the patient's head and the plurality of electrodes are capable of receiving and measuring one or more signals representative of brain activity;

a plurality of transmitting wires incorporated into the support structure; and a wireless transmitter, where each of the plurality of transmitting wires is operably connected between a respective electrode and the wireless transmitter.

12. The system of claim 11, wherein the plurality of transmitting wires are directly connected to the wireless transmitter.

13. The system of claim 11, further comprising a connector, wherein the connector operably connects the plurality of transmitting wires to the wireless transmitter.

14. The system of claim 11, further comprising a neurodiagnostic device, wherein the wireless transmitter is capable of transmitting the one or more signals to the neurodiagnostic device.

15. The system of claim 14, wherein the neurodiagnostic device is configured to display information corresponding to the one or more signals.

16. The system of claim 14, wherein the device comprises another wireless transmitter configured to transmit the one or more signals received by the neurodiagnostic device or additional information to a remote location.

17. The system of claim 11, wherein each of the plurality of electrodes are positioned at predetermined locations on the support structure.

18. The system of claim 11, wherein each of the plurality of electrodes is detachably coupled to the support structure.

19. The system of claim 11, wherein the support structure is adapted to cover at least predetermined areas of the patient's head when it is mounted on the patient's head.

20. The system of claim 11, further comprising an impedance meter configured to verify the proper connection of the plurality of electrodes to the patient's head.

* * * * *